United States Patent
Wagner

[11] Patent Number: 5,391,350
[45] Date of Patent: Feb. 21, 1995

[54] APPARATUS AND METHOD FOR STERILIZING CONTAINERS IN AN AUTOCLAVE

[75] Inventor: Jeffrey R. Wagner, Shortsville, N.Y.

[73] Assignee: Nalge Company, Rochester, N.Y.

[21] Appl. No.: 208,639

[22] Filed: Mar. 9, 1994

[51] Int. Cl.⁶ .............................................. A61L 2/06
[52] U.S. Cl. ....................................... 422/26; 422/33; 422/1; 422/294; 422/295
[58] Field of Search ....................... 422/1, 26, 33, 292, 422/294, 295; 206/216, 439; 215/100 R, 228; 220/212; 435/31, 294, 295, 297, 298, 810

[56] References Cited

U.S. PATENT DOCUMENTS

| | | | |
|---|---|---|---|
| 3,630,665 | 12/1971 | Andersen et al. | 422/33 |
| 4,283,498 | 8/1981 | Schlesinger | 435/810 |
| 4,588,561 | 5/1986 | Aswell et al. | 435/810 |
| 4,943,414 | 7/1990 | Jacobs et al. | 422/294 |

Primary Examiner—Robert J. Warden
Assistant Examiner—T.A. Trembley
Attorney, Agent, or Firm—Wood, Herron & Evans

[57] ABSTRACT

A sterilizable system and method for sterilizing containers in an autoclave. The system includes a container, closure bag, and fastener. The closure is placed in the interior of the bag, and the opening of the container is put into the interior of the bag through the bag's opening. The closure and container are kept in non-sealing relationship, and the sterilizable system is completed by fastening the opening of the bag around the container with the fastener. Once the system is sterilized, the user seals the container and closure by grasping the bag and manipulating the closure into sealing relationship with the container. The user then removes the fastener and bag, leaving a sterilized container.

17 Claims, 1 Drawing Sheet

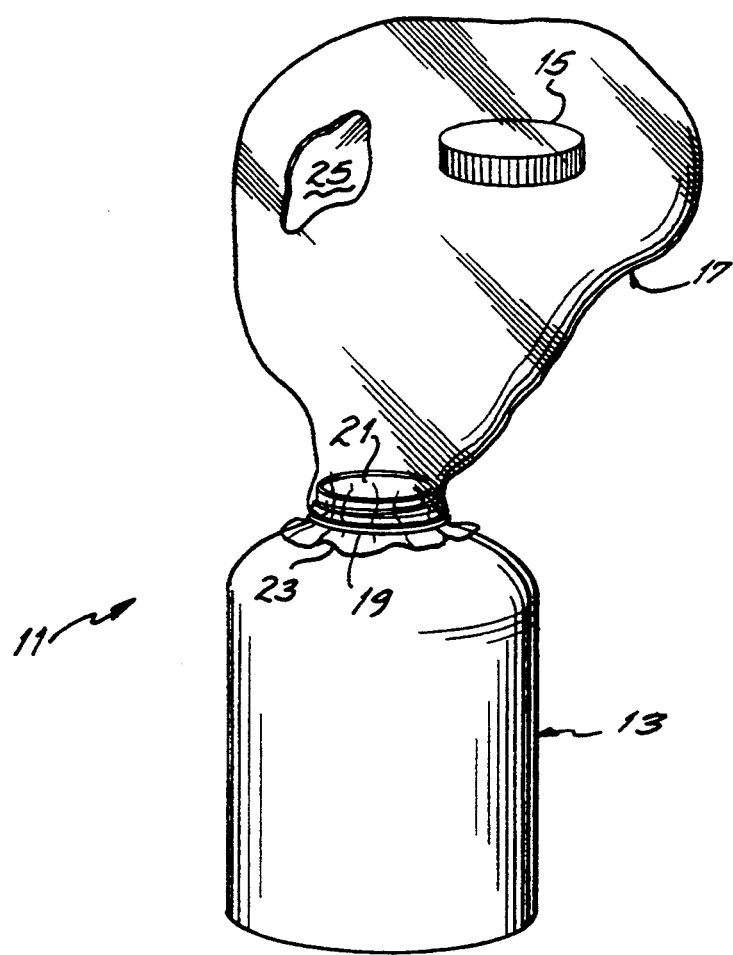

APPARATUS AND METHOD FOR STERILIZING CONTAINERS IN AN AUTOCLAVE

BACKGROUND OF THE INVENTION

This invention relates to the sterilization of containers, and more particularly, to a system of components as well as a method for sterilizing containers in an autoclave.

In many industries and applications, it is desirable to reuse various containers in order to lower costs and reduce waste. In several of these applications, it is important and even essential to sterilize the containers between each use.

One popular method of sterilization is autoclaving, in which a container and it's component parts such as a closure or lid are placed in an autoclave, which then uses superheated steam under pressure to sterilize the contents. Although the autoclave is an effective sterilizer, standard autoclaving techniques have several limitations and disadvantages. For example, if a container and closure to be sterilized are sealed before being placed in the autoclave, they will deform or implode under the pressure of the autoclave sterilization process. Another option is to separate the container and closure before placing them in the autoclave. However, this method introduces additional problems. Unless the autoclave and containers are being used in a sterile room, the sterilized container and closure will become contaminated when they are removed from the autoclave. In most applications such a sterile operating environment is impractical.

Therefore, it is desirable to have an apparatus and method for sterilizing containers and their closures or lids in an autoclave, without having the problems of deformation, implosion and contamination.

SUMMARY OF THE INVENTION

It is an object of the present invention to provide an apparatus for sterilizing containers and closures in an autoclave so that the containers do not implode or deform during the autoclaving process, and so that the interior surfaces of the containers and closures remain sterile when removed from the autoclave.

It is a further object of the present invention to provide a method for sterilizing containers in an autoclave to avoid the problems of implosion and deformation, while maintaining sterility of the containers when they are removed from the autoclave.

To these ends, the invention includes a sterilizable system, kit of components and method of sterilization in an autoclave. The sterilizable system and kit include a container having an opening, a closure capable of covering that opening, a bag with an interior and having an opening, and a fastener. In forming the sterilizable system or performing the method of this invention, the closure is placed in the interior of the bag, and the opening of the container is put into the interior of the bag through the bag's opening. The closure and the container are kept in a non-sealing relationship, and the sterilizable system is completed by fastening the opening of the bag around the container with the fastener.

This sterilizable system then is ready for sterilization in an autoclave. Once the system has been sterilized, the user may seal the container and closure by grasping the bag and manipulating the closure while the closure and container opening are still within the interior of the bag. Once the container is sealed, the fastener and bag may be removed, leaving a sterilized container.

The components (container, closure, bag and fastener) of the sterilizable system may be made of any materials capable of withstanding autoclave conditions. Preferably, the materials should be capable of withstanding conditions of steam heat at about 250° C. for about twenty minutes.

In one form of the invention, the bag is made of a hydrocarbon or fluorocarbon polymer such as ethylenetetrafluoroethylene, fluorinated ethylene propylene, fluorinated polypropylene, polyallomer, polycarbonate, alkoxylated polytetrafluoroethylene, polypropylene, or thermoplastic elastomer.

Typically, the container is made of ceramic, glass, metal, or plastic. If plastic is used, the preferred material is a hydrocarbon or fluorocarbon polymer such as ethylenetetrafluoroethylene, fluorinated ethylene propylene, fluorinated polypropylene, polyallomer, polycarbonate, alkoxylated polytetrafluoroethylene, polypropylene, or thermoplastic elastomer.

Similar to the other components of the sterilizable system, the fastener may be made of any autoclavable material. In the preferred form of the sterilizable system, however, the fastener is made of plastic or rubber.

One of the primary advantages of the sterilizable system and method of this invention is the ability to sterilize a container in an autoclave without having the container implode or deform under the stresses of the autoclave conditions. Another advantage of the invention is that sterility is preserved when the container is removed from the autoclave.

These and other objectives and advantages will become apparent to one skilled in the art from the following detailed description of a preferred embodiment and from the drawing.

BRIEF DESCRIPTION OF DRAWING

The Figure is an elevational view of a sterilizable system for sterilizing a container and closure in an autoclave.

DETAILED DESCRIPTION OF THE INVENTION

A sterilizable system 11 is shown in the Figure. The sterilizable system 11 includes a container 13, a closure 15, a bag 17, and a fastener 19. The container 13 includes an opening 21, and the bag 17 includes an opening 23 and an interior 25.

In forming the sterilizable system 11 or performing the method of this invention, the closure 15 is placed in the interior 25 of the bag 17, and the opening 21 of the container 13 is put into the interior 25 of the bag 17 through the bag's opening 23. The closure 15 and the container 13 are kept in a non-sealing relationship, and the sterilizable system 11 is completed by fastening the opening 23 of the bag 17 around the container 13 with the fastener 19. Nonsealing relationship means any relationship between the container 13 and closure 15 where these two components are not sealed tightly against one another. Therefore, the invention may be practiced with the closure 15 either loosely on or off the container 13. In the preferred mode of this invention, the closure 15 will be fully disengaged from the container 13 as in the Figure.

The sterilizable system 11 then is ready for sterilization in an autoclave. Once the system 11 has been sterilized, the user may seal the container 13 and closure 15 by grasping the bag 17 and manipulating the closure 15 while the closure 15 and container opening 21 are still within the interior 25 of the bag 17. Once the container 13 and closure 15 are sealed, the fastener 19 and bag 17 may be removed, leaving a sterilized container 13 and closure 15.

The components (container, closure, bag, and fastener) of the sterilizable system may be made of any materials capable of withstanding autoclave conditions. Preferably, the materials should be capable of withstanding conditions of steam heat at about 250 ° C. for about twenty minutes.

In one form of the invention, the bag is made of a hydrocarbon or fluorocarbon polymer such as ethylenetetrafluoroethylene, fluorinated ethylene propylene, fluorinated polypropylene, polyallomer, polycarbonate, alkoxylated polytetrafluoroethylene, polypropylene, or thermoplastic elastomer. In the best mode of the invention, the material selected allows the bag to be reused in subsequent container sterilizations.

Typically, the container is made of ceramic, glass, metal, or plastic. If plastic is used, the preferred material is a hydrocarbon or fluorocarbon polymer such as ethylenetetrafluoroethylene, fluorinated ethylene propylene, fluorinated polypropylene, polyallomer, polycarbonate, alkoxylated polytetrafluoroethylene, polypropylene, or thermoplastic elastomer.

As with the other components of the sterilizable system, the fastener may be made of any autoclavable material. In the preferred form of the sterilizable system, the fastener is made of plastic or rubber. If desired, the fastener may be permanently attached to the bag. For example, the fastener may surround the opening of the bag and be held within a hem.

For convenience, the container, closure, bag and fastener may be shipped in unassembled form as a kit or kits, and do not have to be assembled as a sterilizable system in order to come within the scope of the invention.

The sterilizable system, kit of components, and method of this invention offer several advantages. One of the primary advantages is the ability to sterilize a container in an autoclave without having the container implode or deform under the stresses of the autoclave conditions. Another advantage of the invention is that interior container sterility is preserved when the container is removed from the autoclave, without having to operate in a sterile room.

This invention is not limited to the description discussed above, but on the contrary, is intended to cover the various modifications and equivalent arrangements included within the spirit and scope of the appended claims.

What is claimed is:

1. A sterilizable system for sterilizing a container and closure in an autoclave comprising:
    a container having an opening,
    a closure capable of covering said opening of said container,
    a bag with an interior and having an opening, said closure disposed within said interior of said bag in nonsealing relationship to said container opening, said container opening being inserted into said bag interior through said bag opening, and
    a fastener securing said bag opening in encircling relation to said container opening to form a sterilizable system for sterilization in an autoclave.

2. The sterilizable system of claim 1 wherein said container, said closure, said bag and said fastener are capable of withstanding autoclave conditions of steam heat at about 250° C. for about 20 minutes.

3. The sterilizable system of claim 1 wherein said bag is made of a plastic selected from the group consisting essentially of ethylenetetrafluoroethylene, fluorinated ethylene propylene, fluorinated polypropylene, polyallomer, polycarbonate, alkoxylated polytetrafluoroethylene, polypropylene, and thermoplastic elastomer.

4. The sterilizable system of claim 1 wherein said container and closure are made from a material selected from the group consisting of plastic, ceramic, glass, and metal.

5. The sterilizable system of claim 4 wherein said plastic is selected from the group consisting essentially of ethylenetetrafluoroethylene, fluorinated ethylene propylene, fluorinated polypropylene, polyallomer, polycarbonate, alkoxylated polytetrafluoroethylene, polypropylene, and thermoplastic elastomer.

6. The sterilizable system of claim 1 wherein said fastener is an elastic band.

7. The sterilizable system of claim 1 wherein said fastener is plastic.

8. A method of sterilizing a container and closure in an autoclave comprising:
    providing a container having an opening, a closure capable of sealing said opening of said container, a bag with an interior and having an opening, and a fastener,
    placing said closure within said interior of said bag in nonsealing relationship to said opening of said container,
    placing said opening of said container into said interior of said bag through said bag opening,
    forming a sterilizable system by fastening said opening of said bag in encircling relation to said container opening using said fastener with said closure located within said bag interior, and
    maintaining said sterilizable system in an autoclave until said sterilizable system is sterilized.

9. The method of claim 8 further including the step of:
    placing said closure in sealing relationship to said opening of said container while said container opening and said closure are still within said interior of said bag.

10. The method of claim 9 wherein said step of sealing said container opening with said closure occurs while said bag opening is fastened around said container with said fastener, said method including the further step of removing said sealed container opening from said bag following said container sealing step.

11. The method of claim 8 wherein said container, said closure, said bag and said fastener are capable of withstanding autoclave conditions of steam heat at about 250° C. for about 20 minutes.

12. The method of claim 8 wherein said bag is made of a plastic selected from the group consisting essentially of ethylenetetrafluoroethylene, fluorinated ethylene propylene, fluorinated polypropylene, polyallomer, polycarbonate, alkoxylated polytetrafluoroethylene, polypropylene, and thermoplastic elastomer.

13. The method of claim 8 wherein said container and closure are made from a material selected from the group consisting of plastic, ceramic, glass, and metal.

14. The method of claim 13 wherein said plastic is selected from the group consisting essentially of ethylenetetrafluoroethylene, fluorinated ethylene propylene, fluorinated polypropylene, polyallomer, polycarbonate, alkoxylated polytetrafluoroethylene, polypropylene, and thermoplastic elastomer.

15. The method of claim 8 wherein said fastener is an elastic band and said fastening step includes placing said elastic band around said bag opening with said container opening inserted into said bag interior through said bag opening.

16. The method of claim 8 wherein said fastener is a plastic fastener and said fastening step includes placing said plastic fastener around said bag opening with said container opening inserted into said bag interior through said bag opening.

17. The method of claim 8 wherein said system is maintained in said autoclave with steam heat at about 250° C. for about 20 minutes.

* * * * *